(12) United States Patent
Kunz et al.

(10) Patent No.: US 6,498,265 B2
(45) Date of Patent: Dec. 24, 2002

(54) 3-AMINO-2-MERCAPTOBENZOIC ACID DERIVATIVES AND PROCESSES FOR THEIR PREPARATION

(75) Inventors: Walter Kunz, Oberwil (CH); Beat Jau, Aesch (CH)

(73) Assignee: Syngenta Investment Corporation, Wilmington, DE (US)

(*) Notice: Subject to any disclaimer, the term of this patent is extended or adjusted under 35 U.S.C. 154(b) by 0 days.

(21) Appl. No.: 09/963,046

(22) Filed: Sep. 25, 2001

(65) Prior Publication Data

US 2002/0040157 A1 Apr. 4, 2002

Related U.S. Application Data

(60) Continuation of application No. 09/259,897, filed on Feb. 26, 1999, now Pat. No. 6,380,422, which is a division of application No. 09/148,276, filed on Sep. 4, 1998, now Pat. No. 6,002,013.

(30) Foreign Application Priority Data

Dec. 21, 1995 (CH) ................................................ 3637/95

(51) Int. Cl.⁷ ..................... C07C 327/00; C07C 321/06; C07C 327/16
(52) U.S. Cl. ........................... 558/257; 560/18; 562/26; 562/432
(58) Field of Search ..................... 562/432, 26; 560/18; 558/257

(56) References Cited

U.S. PATENT DOCUMENTS

| 4,851,037 A | 7/1989 | Borengo et al. |
| 5,190,928 A | 3/1993 | Schurter et al. |
| 5,268,389 A | 12/1993 | Harrison et al. |
| 5,374,737 A | 12/1994 | Dapperheld et al. |

FOREIGN PATENT DOCUMENTS

| DE | 2751441 | 6/1978 |
| DE | 2757924 | 7/1979 |
| EP | 0 384 889 | 8/1990 |
| JP | 06090518 | 10/1995 |
| WO | WO96/11906 | 4/1996 |

OTHER PUBLICATIONS

Allen et al., "2–Amino–6–methylbenzothiazole", Organic Synthesis Collective vol. 3, pp. 76–79 (1955).
Gupta et al., "Studies on Phenothiazines. Part 7(1). Synthesis of 3–Substituted 2–Aminobenzothiazoles and their Conversion to Phenothiazines" J. Heterocyclic Chem. vol. 17, pp. 1325–1327, (1980).
Gupta et al., "Synthesis of 2–amino–3–Fluorobenzenethiol and its Conversion into Different Heterocycles" Synthesis Communications, vol. 17(2), pp. 229–240 (1987).
Haddock et al., "1,2,3–Benzothiadiazoles Part V. The Rearrangement of Diazonium Salts derived from 7–Aminobenzisothiazoles" J Chem Soc (c) pp. 3994–3998 (1971).
Kirby et al., 1,2,3–Benzothiadiazoles part 1. A Simplified Synthesis of 1,2,3–Benzothiadiazoles J Chem Soc (c) pp. 2250–2253 (1970).
Ukraine, Kim Zhur (1956) vol. 22, pp. 363–367 (as cited in Chem Abstr (1957) vol. 51, #22 4358b).

*Primary Examiner*—Cecilia Tsang
*Assistant Examiner*—Ebenezer Sacket
(74) *Attorney, Agent, or Firm*—William A. Teoli, Jr.; Thomas Hamilton

(57) ABSTRACT

Compounds of the formula I

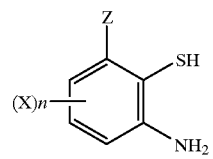

I and disulfides thereof and salts thereof are important intermediate products for the preparation of compounds having a microbicidal and plant-immunizing action, of the formula III

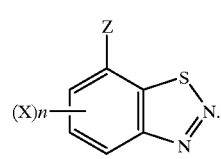

III

In the compounds of the formulae I and III:
X is halogen,
n is 0,1,2 or 3;
Z is CN, CO—A or CS—A,
A is hydrogen, halogen, $OR_1$, $SR_2$ and $N(R_3)R_4$;
$R_1$ to $R_4$ are hydrogen, a substituted or unsubstituted, open-chain, saturated or unsaturated hydrocarbon radical containing not more than 8 carbon atoms, a substituted or unsubstituted cyclic, saturated or unsaturated hydrocarbon radical containing not more than 10 carbon atoms, substituted or unsubstituted benzyl or phenethyl, a substituted or unsubstituted alkanoyl group containing not more than 8 carbon atoms, a substituted or unsubstituted benzoyl group or a substituted or unsubstituted heterocyclyl radical; or $R_3$ and $R_4$, together with the nitrogen atom to which they are bonded, are a 5- or 6-membered, substituted or unsubstituted heterocyclic radical having 1–3 heteroatoms O, S and/or N.

Processes for the preparation of compounds of the formula I are described.

11 Claims, No Drawings

3-AMINO-2-MERCAPTOBENZOIC ACID DERIVATIVES AND PROCESSES FOR THEIR PREPARATION

The present application is a continuation of U.S. Ser. No. 09/259,897, filed Feb. 26, 1999 now U.S. Pat. No. 6,380,422, which is a divisional of U.S. Ser. No. 09/148,276, filed Sep. 4, 1998 now U.S. Pat. No. 6,002,013.

3-Amino-2-mercaptobenzoic Acid Derivatives and Processes for Their Preparation

The invention relates to a compound of the formula I

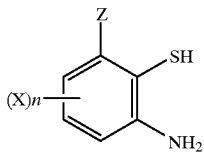

I and the disulfide thereof and salts thereof, processes for the preparation thereof and the use thereof for the preparation of compounds having a microbicidal and plant-immunizing action, of the formula III

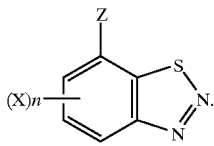

III

In the compounds of the formulae I and III:
X is halogen,
n is 0,1,2 or 3;
Z is CN, CO—A or CS—A,
A is hydrogen, $OR_1$, $SR_2$ and $N(R_3)R_4$;
$R_1$ to $R_4$ are hydrogen, a substituted or unsubstituted, open-chain, saturated or unsaturated hydrocarbon radical containing not more than 8 carbon atoms, a substituted or unsubstituted cyclic, saturated or unsaturated hydrocarbon radical containing not more than 10 carbon atoms, substituted or unsubstituted benzyl or phenethyl, a substituted or unsubstituted alkanoyl group containing not more than 8 carbon atoms, a substituted or unsubstituted benzoyl group or a substituted or unsubstituted heterocyclyl radical; or $R_3$ and $R_4$, together with the nitrogen atom to which they are bonded, are a 5- or 6-membered, substituted or unsubstituted heterocyclic radical having 1–3 heteroatoms O, S and/or N.

The compounds of the formula I have at least one basic group and can thus form acid addition salts. These are formed, for example, with mineral acids, for example sulfuric acid, a phosphoric acid or a hydrogen halide acid, with organic carboxylic acids, for example acetic acid or oxalic, malonic, maleic, fumaric or phthalic acid, with hydroxycarboxylic acids, for example ascorbic, lactic, malic, tartaric or citric acid, or with benzoic acid, or with organic sulfonic acids, for example methane- or p-toluenesulfonic acid. On the basis of the SH group or an acid group in the substituent Z, compounds of the formula I can furthermore form salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propyl-amine, or a mono-, di- or trihydroxy-lower alkylamine, for example mono-, di- or triethanolamine. If appropriate, corresponding inner salts can furthermore be formed.

Unless defined otherwise, the general terms used above and below have the meanings given below:

Hydrocarbon radicals can be saturated or unsaturated and open-chain or cyclic, or a mixture of open-chain and cyclic, for example cyclopropylmethyl or benzyl.

Alkyl groups are straight-chain or branched, depending on the number of carbon atoms, and are, for example, methyl, ethyl, n-propyl, iso-propyl, n-butyl, sec-butyl, iso-butyl, tert-butyl, sec-amyl, tert-amyl, 1-hexyl or 3-hexyl.

Unsaturated hydrocarbon radicals are alkenyl, alkynyl or alkenynyl groups with at least 3 multiple bonds, for example butadienyl, hexatrienyl, 2-penten-4-ynyl.

Alkenyl is to be understood as meaning straight-chain or branched alkenyl, for example allyl, methallyl, 1-methylvinyl or but-2-en-1-yl. Alkenyl radicals with a chain length of 3 to 4 carbon atoms are preferred.

Alkynyl can likewise be straight-chain or branched, depending on the number of carbon atoms, for example propargyl, but-1-yn-1-yl and but-1-yn-3-yl. Propargyl is preferred.

Cyclic unsaturated hydrocarbon radicals can be aromatic, for example phenyl and naphthyl, or non-aromatic, for example cyclopentenyl, cyclohexenyl, cycloheptenyl and cyclooctadienyl, or partly aromatic, for example tetrahydronaphthyl and indanyl.

Halogen or halo and Hal are fluorine, chlorine, bromine or iodine, preferably fluorine, chlorine or bromine.

Haloalkyl can contain identical or different halogen atoms, for example fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl and 3,3,3-trifluoropropyl.

Alkoxy is, for example, methoxy, ethoxy, propyloxy, i-propyloxy, n-butyloxy, iso-butyloxy, sec-butyloxy and tert-butyloxy; preferably methoxy and ethoxy.

Haloalkoxy is, for example, difluoromethoxy, trifluoromethoxy, 2,2,2-trifluoroethoxy, 1,1,2,2-tetrafluoroethoxy, 2-fluoroethoxy, 2-chloroethoxy and 2,2-difluoroethoxy.

Cycloalkyl is cyclopropyl, cyclobutyl, cyclopentyl or cyclohexyl.

Alkanoyl is either straight-chain or branched. Examples are formyl, acetyl, propionyl, butyryl, pivaloyl or octanoyl.

A heterocyclyl radical is understood as meaning 5- or 6-membered aromatic and non-aromatic rings with heteroatoms N, O and/or S. An unsubstituted or substituted benzo group can furthermore be fused onto such a heterocyclyl radical bonded to the remainder of the molecule. Examples of heterocyclyl groups are pyridyl, pyrimidinyl, imidazolyl, thiazolyl, 1,3,4-thiadiazolyl, triazolyl, thienyl, furanyl, pyrrolyl, morpholinyl, oxazolyl and the corresponding partly or totally hydrogenated rings. Examples of heterocyclyl groups with a fused-on benzo group are quinolyl, isoquinolyl, benzoxazolyl, quinoxalinyl, benzothiazolyl, benzimidazolyl, indolyl and indolinyl.

Compounds of the formula III having a microbicidal and plant-immunizing action and processes for the preparation thereof are known, for example, from EP-A-313,512. The processes described therein are not suitable for industrial preparation, since they comprise many reaction stages, some of which are complex, and thus overall result in an unsatisfactory yield.

There is therefore a need for a novel, industrially more advantageous synthesis for such compounds.

The compounds of the formula I according to the invention allow a novel access to the compounds of the formula III, which is shown in Equation 1. This synthesis is distinguished by easy accessibility of the percursor, use of customary reactants and good yields, even in cases where an intermediate product is not isolated.

The present invention likewise relates to this synthesis.

In the formulae of Equation 1,

X, n and Z are as defined for formula I and

T is hydrogen, $C_1$–$C_{12}$alkyl, in particular $C_1$–$C_6$alkyl, $C_3$–$C_6$alkenyl, $C_3$–$C_6$alkynyl, $C_3$–$C_6$cycloalkyl or substituted or unsubstituted phenyl, benzyl or phenethyl.

The precursors of the formula V are compounds which are obtainable industrially or can be prepared by known methods, for example by reduction of the corresponding nitro compounds.

Equation 1

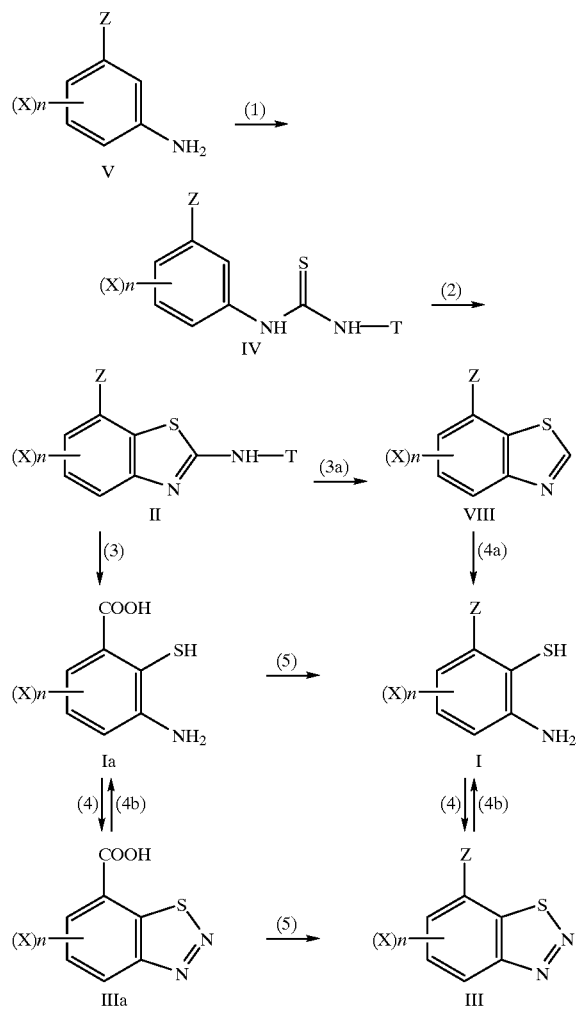

In detail, the reaction stages can be carried out as follows:
(1) SCN-T/for example methyl isothiocyanate/inert solvent/ if appropriate in the presence of acid or base; or SCN salt.
(2) Oxidizing agent, for example $SO_2Cl_2$ or $Br_2$ or $H_2SO_4$/bromide or $Cl_2$.
(3) Strong aqueous base, for example potassium hydroxide solution, preferably under an inert atmosphere.

Reactions (1), (2) and (3) as such are described, for example, in

Org. Synthesis, Coll.Volume III, page.76;
J.Het.Chem. Volume 17, page 1325, (1980);
U.S. Pat. No. 5,374,737;
Ukrain.Khim.Zhur. Volume 22, 363, 1956; cited in Chem.Abstr. 22, 4358b, (1957).
(3a) Diazotization/$H_3PO_2$(Synth. Comm. Volume 10, page 167 1980)
(4) Diazotization with cyclization, for example with nitrous acid (=HONO) or with an inorganic or organic nitrite, for example sodium nitrite or isoamyl nitrite (for example EP A 313,512).
(4a) For example hydrazine/ethanol or basic hydrolysis, or such as 4) (Synth. Comm. Volume 10, page 167 1980).
(4b) For example Zn/acid or Fe/acid (Heterocyclic Compounds, Volume 7, page 541 et seq.); or $H_2$/catalyst
(5) The conversion of the group COOH into a group Z where Z is as defined for formula I can be carried out by known methods, as shown in Equation 2.

Preferred compounds of the formula I are
(1) Compounds in which:
X is fluorine;
n is 0,1,2or3;
Z is CN, CO—A or CS—A,
A is $OR_1$, $SR_2$ or $N(R_3)R_4$; and in which
$R_1$, $R_2$ and $R_3$ are hydrogen, $C_1$–$C_8$alkyl, which is unsubstituted or substituted by 1–5 halogen atoms, $C_3$–$C_6$cycloalkyl, $C_1$–$C_4$alkoxy, phenoxy, benzyloxy $C_1$–$C_4$acyloxy, benzoyloxy, hydroxyl, nitro, cyano, $C_1$–$C_4$alkanoyl, benzoyl, carboxyl, $C_1$–$C_4$alkoxycarbonyl, benzyloxycarbonyl, amino, $C_1$–$C_4$alkylamino, $C_1$–$C_4$dialkylamino or heterocyclyl, $C_3$–$C_6$alkenyl which is unsubstituted or substituted by 1–5 halogen atoms, $C_3$–$C_6$alkynyl, $C_3$–$C_6$cycloalkyl, $C_1$–$C_4$alkanoyl, phenyl, benzyl or phenethyl, the phenyl rings of which are unsubstituted or substituted once to three times by halogen, hydroxyl, $C_1$–$C_4$alkyl, halogeno-$C_1$–$C_2$alkyl, $C_1$–$C_2$alkoxy, halogeno-$C_1$–$C_2$alkoxy or nitro, or naphthyl, benzoyl or heterocyclyl, which are unsubstituted or substituted once to three times in an identical or different manner by halogen, $C_1$–$C_2$alkyl, halogenomethyl or nitro, or
$R_4$ is hydrogen, Cl–$C_6$alkyl, phenyl or benzyl; or
$R_3$ and $R_4$, together with the nitrogen atom to which they are bonded, are a 5- or 6-membered ring with 1–2 heteroatoms O,S and/or N, where the rings mentioned are unsubstituted or substituted once or twice in an identical or different manner by halogen, $C_1$–$C_3$alkyl or $C_1$–$C_2$alkoxycarbonyl.
(2) Compounds in which:
X is fluorine;
n is 0 or 1;
Z is CN or CO—A,
A is $OR_1$, $SR_2$ or $N(R_3)R_4$; and in which
$R_1$ to $R_4$ are as defined for claim 2.
(3) Compounds in which:
X is fluorine;
n is 0 or 1;
Z is CN or CO—A,
A is $OR_1$ or $SR_2$; and
$R_1$ and $R_2$ are hydrogen, $C_1$–$C_6$alkyl, which is unsubstituted or substituted by 1–3 halogen atoms, $C_3$–$C_6$cycloalkyl or $C_1$–$C_2$alkoxy, $C_3$–$C_4$alkenyl, which is unsubstituted or substituted by 1–3 halogen atoms, $C_3$–$C_4$alkynyl, $C_3$–$C_6$cycloalkyl or phenyl, benzyl or phenethyl, the phenyl rings of which are unsubstituted or substituted once or twice by halogen, hydroxyl, $C_1$–$C_4$alkyl, halogeno-$C_1$–$C_2$alkyl, $C_1$–$C_2$alkoxy, halogeno-$C_1$–$C_2$alkoxy or nitro.

(4). The compound of the formula Ia1 or the disulfide thereof or a salt thereof

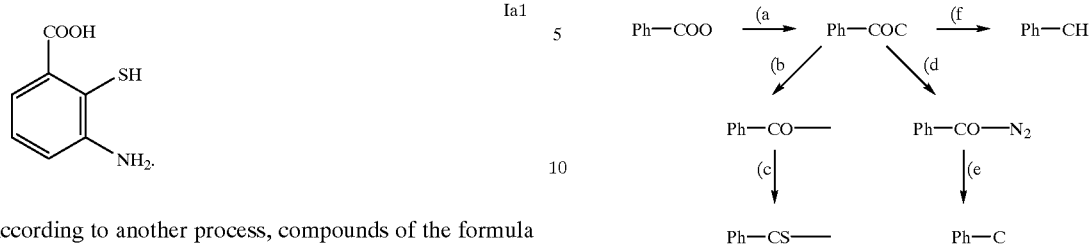

According to another process, compounds of the formula I can be prepared in accordance with Equation 2 via the corresponding benzodithiazolium salts VI or hydroxybenzodithiazoles VII (Houben-Weyl, E8d, Heteroarene [Heteroarenes] III, Part 4; page 2 et seq. and page 59 et seq.).

Equation 2

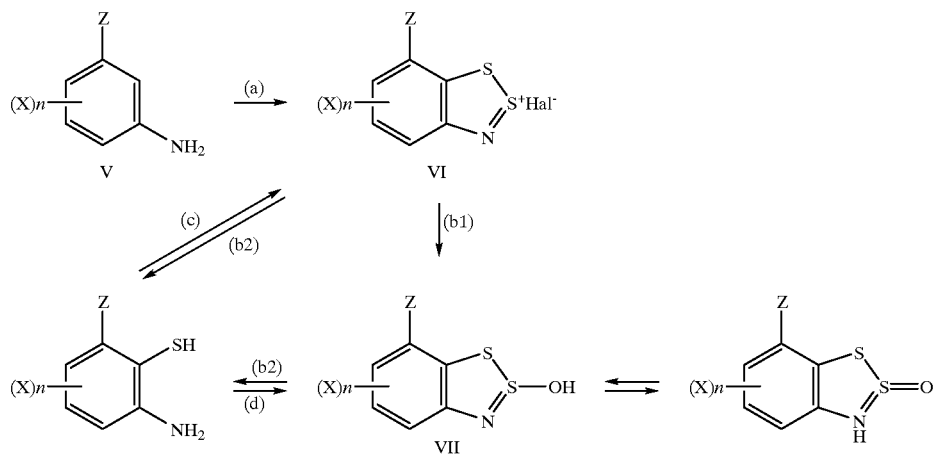

I or
Ia (Z = COOH)

(a) Sulfur halide, for example $S_2Cl_2$ or $SCl_2$ (where the aniline derivative V is primarily preferably converted into the corresponding hydrochloride salt) in an inert solvent, for example acetic acid, at 0–120° C. (J. Org. Chem. 30, 2763, J. Het. Chem 3,518, ibid 5, 1149)

(b1) $H_2O$/or $H_2O$/NaOAc (0–50° C.) (Khim. Get. Soed. (9), 1205 (1979); Synth. Comm. 23, 263)

(b2) $H_2O$/20–100° C. with or without a base, such as sodium bicarbonate, sodium carbonate or dilute alkali metal or alkaline earth metal hydroxide or oxide (J. Am. Chem. Soc. 68, 1594 (1946))

(c) Sulfur dihalide (for example $SCl_2$), thionyl halide ($SOCl_2$)–20 to 100° C. (J. Het. Chem. 3, 518), (d) $S(O)L_2$, where L is a leaving group, such as halogen, imidazol-1'-yl or 1,2,4-triazol-1-yl, for example thionyldiimidazol or $SOCl_2$, −30 to 100° C., inert solvent (J. Org. Chem. 30, 2763 (1965)).

The benzodithiazolium salts VI and VII can also be further reacted in situ, without isolation and under suitable conditions (J. Chem. Soc. 1970, 2250, Houben Weyl E8d, Heteroarene [Heteroarenes] III, Part 4, page 59 et seq. (specifically page 93 et seq.)), to give benzothiadiazoles III or IIIa.

Equation 3: Conversion of the group z $$Ph-COO \xrightarrow{(a)} Ph-COC \xrightarrow{(f)} Ph-CH$$
$$(b) \swarrow \qquad \searrow (d)$$
$$Ph-CO- \qquad Ph-CO-N_2$$
$$(c) \downarrow \qquad \downarrow (e)$$
$$Ph-CS- \qquad Ph-C$$

-continued

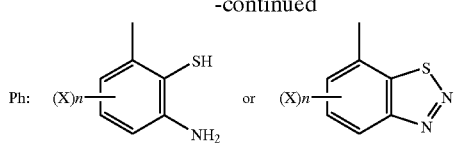

(a) Chlorinating agent, for example $SOCl_2$ or $COCl_2$;
(b) M-A(III), in which M is hydrogen, $Li^+$, $Na^+$, $K^+$, ½ $Mg^{2+}$ or a quaternary ammonium ion and A is as defined for formula I;
(c) Thionating agent, for example phosphorus pentasulfide or 4-methoxyphenylthio-phosphonic acid cyclodithioanhydride ("Lawesson's reagent");
(d) $NH_3$;
(e) Dehydrating agent, for example $SOCl_2$; or $COCl_2$;
(f) Reduction, for example with hydrogen/catalyst, or with a complex hydride, for example $LiAlH_2(OCH_2CH_2OCH_3)_2$.

The reactions described are carried out in a manner known per se, for example in the absence or, usually, in the presence of a suitable solvent or diluent or of a mixture thereof, the reaction being carried out, as required, with cooling, at room temperature or with heating, for example in a temperature range from about −80° C. up to the boiling point of the reaction medium, preferably from about −20° C.

to about +170° C., and, if necessary, in a closed vessel, under pressure, in an inert gas atmosphere and/or under anhydrous conditions. Diazotizations, i.e. the reaction of a primary amine with nitrous acid or with an inorganic or organic nitrite, are advantageously carried out at −20° C. to +30° C.

Leaving groups are, for example, fluorine, chlorine, bromine, iodine, $C_1$–$C_8$alkylthio, such as methylthio, ethylthio or propylthio, $C_1$–$C$alkanoyloxy, such as acetoxy, (halogeno)-$C_1$–$C_8$ alkanesulfonyloxy, such as methanesulfonyloxy, ethanesulfonyloxy or trifluoromethanesulfonyloxy, or substituted or unsubstituted phenylsulfonyloxy, such as benzenesulfonyloxy or p-toluenesulfonyloxy, imidazolyl, triazolyl, hydroxyl or water, preferably chlorine, bromine, iodine and p-toluenesulfonyloxy.

Suitable bases are, for example, alkali metal or alkaline earth metal hydroxides, hydrides, amides, alkanolates, carbonates, dialkylamides or alkylsilylamides, alkylamines, alkylenediamines, non-alkylated or N-alkylated, saturated or unsaturated cycloalkylamines, basic heterocyclic compounds, ammonium hydroxides and carbocyclic amines. Examples are sodium hydroxide, hydride, amide, methanolate and carbonate, potassium tert-butanolate and carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyl-trimethyl-ammonium hydroxide and 1,8-diazabicyclo[5.4.0]-undec-5-ene (DBU).

The reactants can be reacted with one another as such, i.e. without addition of a solvent or diluent, for example in the melt. However, the addition of an inert solvent or diluent or of a mixture thereof is usually advantageous. Examples of such solvents or diluents are: aromatic, aliphatic and alicyclic hydrocarbons and halogenated hydrocarbons, such as benzene, toluene, xylene, chlorobenzene, bromobenzene, petroleum ether, hexane, cyclohexane, methylene chloride, chloroform, dichloroethane or trichloroethane; ethers, such as diethyl ether, tert-butyl methyl ether, tetrahydrofuran or dioxane; ketones, such as acetone or methyl ethyl ketones; alcohols, such as methanol, ethanol, propanol, butanol, ethylene glycol or glycerol; esters, such as ethyl acetate or butyl acetate; amides, such as N,N-dimethylformamide, N,N-dimethylacetamide, N-methylpyrrolidone or hexamethylphosphoric acid triamide; nitriles, such as acetonitrile; and sulfoxides, such as dimethyl sulfoxide. Bases employed in excess, such as triethylamine, pyridine, N-methylmorpholine or N,N-diethylaniline, can also be used as solvents or diluents. The reaction can also be carried out under phase transfer catalysis in an organic solvent, for example methylene chloride or toluene, in the presence of an aqueous basic solution, for example sodium hydroxide solution, and a phase transfer catalyst, for example tetrabutylammonium hydrogen sulfate. Typical reaction conditions can be seen from the examples.

The invention furthermore relates to the following preparation processes, in which, in the formulae mentioned under (1) to (6), the substituents are as defined in Equation 1.:

(1) A process for the preparation of a compound of the formula I or a salt thereof.

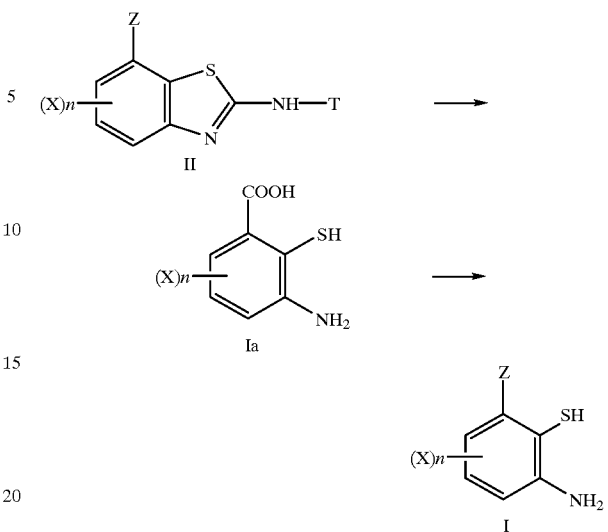

which comprises reacting a compound of the formula II with a strong aqueous base to give a compound of the formula Ia or a salt thereof and further reacting this to give a compound of the formula I.

(2) A process for the preparation of a compound of the formula Ia or a salt thereof

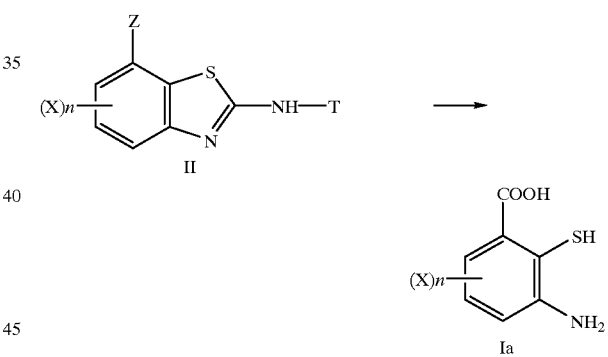

which comprises reacting a compound of the formula II with a strong aqueous base, in particular with potassium hydroxide solution or sodium hydroxide solution, at a temperature of 120–150° C. under a pressure of 1–5 bar.

(3) A process for the preparation of a compound of the formula III

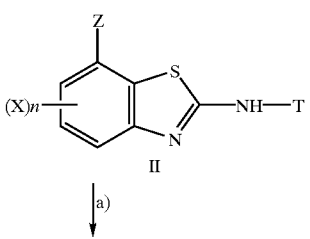

-continued

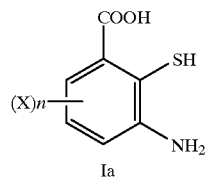
Ia

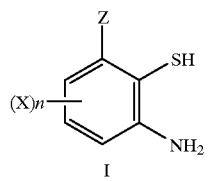
I

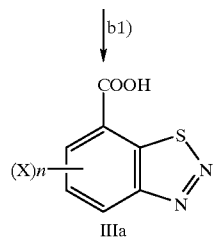
IIIa

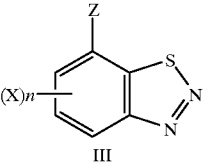
III which comprises a) reacting a compound of the formula II with a strong aqueous base to give a compound of the formula Ia or a salt thereof and, if desired, either
b1) converting it into a compound of the formula III by diazotization with nitrous acid or an organic or inorganic nitrite and, if desired, converting this into a compound of the formula III; or
b2) converting it into a compound of the formula I and converting this into a compound of the formula III by diazotization with nitrous acid or an organic or inorganic nitrite.

(4) A process for the preparation of a compound of the formula IIIa

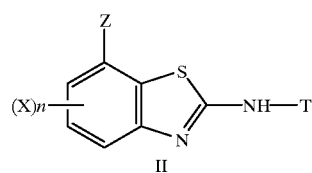
II

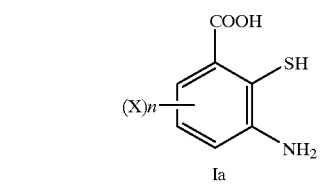
Ia

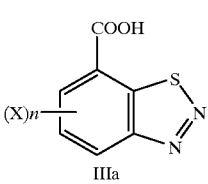
IIIa which comprises reacting a compound of the formula II with a strong aqueous base to give a compound of the formula Ia or a salt thereof and converting this directly, without isolation, into a compound of the formula IIIa by diazotization with nitrous acid or an organic or inorganic nitrite; wherein, in particular, the first reaction stage is carried out in potassium hydroxide solution at 120–170° C. under a pressure of 1–5 bar, and wherein the diazotization is carried out with sodium nitrite.

(5) A process for the preparation of a compound of the formula I

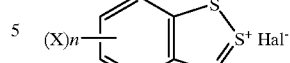

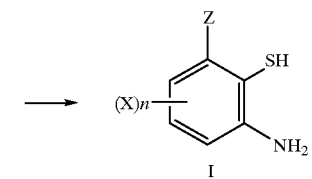
VI → I which comprises hydrolysing a compound of the formula VI under neutral or basic conditions.

(6) A process for the preparation of a compound of the formula II or a salt thereof

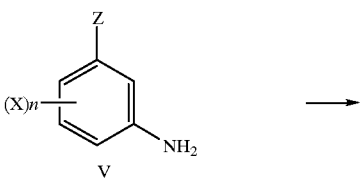
V

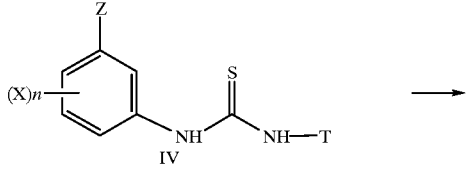
IV

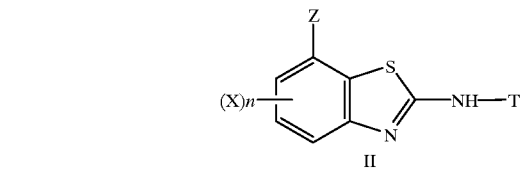
II which comprises reacting a compound of the formula V with SCN-T or with an SCN salt in a solvent, if appropriate in the presence of an acid or base, and reacting the compound thus obtained, of the formula IV, with an oxidizing agent, for example $SO_2Cl_2$ or $Br_2$ or $H_2SO_4$/bromide or $Cl_2$, to give a compound of the formula II. A $C_1$–$C_6$alkyl isothiocyanate, in particular methyl isothiocyanate, is preferably used in the first reaction stage; suitable solvents are anhydrous carboxylic acids, for example formic acid and acetic acid; alcohols, for example ethanol and isopropanol, ketones, ethers and halogenated hydrocarbons. The two reaction steps are particularly preferably carried out in the same solvent, for example in acetic acid, and without isolation of the compound IV.

The invention furthermore relates to the novel intermediates of the formulae II, IV and VI

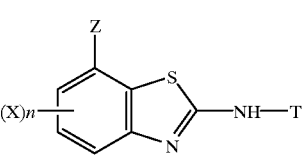
II

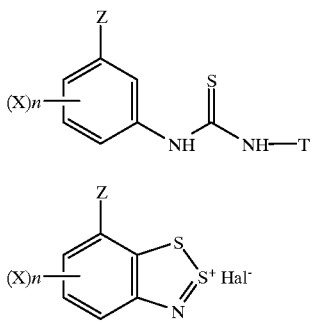

or salts thereof, in which:
X is halogen,
n is 0,1, 2 or 3;
T is hydrogen, $C_1$–$C_6$alkyl, $C_3$–$C_6$alkenyl, $C_3$–$C_6$alkynyl, $C_3$–$C_6$cycloalkyl or substituted or unsubstituted phenyl, benzyl or phenethyl;
Z is CN, CO—A or CS—A,
A is hydrogen, halogen, $OR_1$, $SR_2$ and $N(R_3)R_4$;
$R_1$ to $R_4$ are hydrogen, a substituted or unsubstituted, open-chain, saturated or unsaturated hydrocarbon radical containing not more than 8 carbon atoms, a substituted or unsubstituted cyclic, saturated or unsaturated hydrocarbon radical containing not more than 10 carbon atoms, substituted or unsubstituted benzyl or phenethyl, a substituted or unsubstituted alkanoyl group containing not more than 8 carbon atoms, a substituted or unsubstituted benzoyl group or a substituted or unsubstituted heterocyclyl radical; or $R_3$ and $R_4$, together with the nitrogen atom to which they are bonded, are a 5- or 6-membered, substituted or unsubstituted heterocyclic radical having 1–3 heteroatoms O, S and/or N; and
Hal is halogen, $ClO_4$ or $BF_4$;
with the exception of compounds II and IV, in which Z is $COOC_2H_5$, n is 0 and T is hydrogen (already known from Ukrain.Khim.Zhur. Volume 22, 363, 1956; cited in Chem.Abstr. 22, 4358b, 1957),
and the compound VI, in which Z is $COOCH_3$ and n is 0 (already known from J. Chem. Soc. 1970, 2250, but without being isolated and characterized).
Preferred compounds of the formulae II, IV and VI are those in which:
X is fluorine;
n is 0 or 1;
T is hydrogen or $C_1$–$C_6$alkyl;
Z is CN or CO—A,
A is $OR_1$, $SR_2$ or $N(R_3)R_4$; and in which
$R_1$ to $R_4$ are as defined;
and of these, in particular those in which
A is $OR_1$ or $SR_2$; and
$R_1$ and $R_2$ are hydrogen, $C_1$–$C_6$alkyl, which is unsubstituted or substituted by 1–3 halogen atoms, $C_3$–$C_6$cycloalkyl, or $C_1$–$C_2$alkoxy, $C_3$–$C_4$alkenyl, which is unsubstituted or substituted by 1–3 halogen atoms, $C_3$–$C_4$alkynyl, $C_3$–$C_6$cycloalkyl, or phenyl, benzyl or phenethyl, the phenyl rings of which are unsubstituted or substituted once or twice by halogen, hydroxyl, $C_1$–$C_4$alkyl, halogeno-$C_1$–$C_2$alkyl, $C_1$–$C_2$alkoxy, halogeno-$C_1$–$C_2$alkoxy or nitro; and of these, particularly preferably those in which
n is 0;
T is hydrogen or methyl;
Z is CO—A,
A is $OR_1$; and
$R_1$ is hydrogen, $C_1$–$C_6$alkyl, which is unsubstituted or substituted by 1–3 halogen atoms, or $C_1$–$C_2$alkoxy, $C_3$–$C_6$cycloalkyl, or phenyl, benzyl or phenethyl, the phenyl rings of which are unsubstituted or substituted once or twice by halogen, hydroxyl, $C_1$–$C_4$alkyl, halogeno-$C_1$–$C_2$alkyl, $C_1$–$C_2$alkoxy, halogeno-$C_1$–$C_2$alkoxy or nitro.
In compounds of the formula VI, Hal is preferably chlorine.

PREPARATION EXAMPLES

Example 1:
3-Amino-2-mercapto-benzoic Acid (Ia1)

28.9 g of potassium hydroxide (85%), dissolved in 38 ml of water, are added dropwise to 3.5 g of methyl 2-amino-benzothiazole-7-carboxylate in 38 ml of dioxane under a nitrogen atmosphere in the course of 20 minutes, while stirring and cooling with ice, such that the internal temperature of 25° C. is not exceeded. Thereafter, the mixture is refluxed at a bath temperature of 140° C., and towards the end of the reaction the internal temperature is increased to 170° C. and dioxane is distilled off by means of a descending condenser. The mixture is then cooled to 0° C. and filtered under a nitrogen atmosphere and the residue is rinsed with 30 ml of ice-water. The title compound can be isolated from the filtrate by acidification to pH 5.5, with severe cooling and stirring at a maximum of 0° C., and extraction with ethyl acetate/tetrahydrofuran (8:2) and washing with concentrated sodium chloride solution. Because of the risk of the formation of the disulfide, the potassium salt in the filtrate (potassium 3-amino-2-mercapto-benzoate) is preferably further reacted directly.

Example 2:
Benzo-1,2,3-thiadiazole-7-carboxylic Acid

The filtered aqueous solution, resulting from the above hydrolysis from 17.6 mmol of methyl 2-aminobenzothiazole-7-carboxylate, of the potassium salt of 3-amino-2-mercapto-benzoic acid is rendered acid with 31.6 ml of concentrated sulfuric acid under a nitrogen atmosphere at a maximum of 0° C., while stirring thoroughly and cooling severely, a solution of 1.28 g (18.6 mmol) of sodium nitrite in 3.4 ml of water is added dropwise below the surface at a maximum of 10° C., and the mixture is then stirred for 4 hours, the temperature being allowed to rise to about 25° C. The precipitate formed is filtered off, washed with ice-water and taken up in tetrahydrofuran and, after treatment with active charcoal, the mixture is filtered over a little silica gel. After evaporation of the filtrate, 2.64 g (88% over 2 stages) of the crude title compound of melting point 232–233° C. are obtained. HPLC analysis shows a content of at least 83% of the title compound and about 8–17% of isomeric benzo-1,2,3-thiadiazole-5-carboxylic acid. Recrystallization from dioxane gives the pure title compound of melting point 239–240° C.

Example 3:
Benzo-1,2,3-thiadiazole-7-carbonyl Chloride 290 g of benzo-1,2,3-thiadiazole-7-carboxylic acid are suspended in 1.61 of toluene, 3.5 ml of dimethylformamide and 129 ml of thionyl chloride are added and the mixture is stirred at 80–90° C., the suspension turning into a solution as the release of gas progresses. When the reaction has ended, the solution is cooled and filtered over a little Hyflo, the residue is rinsed with toluene and the filtrate is evaporated. 297 g (93%) of crude acid chloride, which can be further reacted directly, result.

Example 4:
S-Methyl benzo-1,2,3-thiadiazole-7-thiocarboxylate 210 ml of triethylamine and 2.1 g of 4-dimethylaminopyridine are added to a solution of 60.7 g (1.26 mol) of methylmercaptan in 1450 ml of methylene chloride at 0° C. 250.1 g (1.26 mol) of the above acid chloride, dissolved in 1.2 l of methylene chloride, are added dropwise at 0–5° C., while cooling, and the mixture is then stirred to room temperature for 3 hours. Ice-water is then added, the aqueous phase is extracted with methylene chloride and the combined organic extracts are washed with water, dried over sodium sulfate, filtered over a little silica gel and evaporated. 236 g (89%) of S-methyl benzo-1,2,3-thiadiazole-7-thiocarboxylate of melting point 132–134° C. remain.

Example 5:
Methyl 3-amino-benzoate 130 ml (1.78 mol) of thionyl chloride are added dropwise to 500 ml of methanol, which has been cooled to −5° C., while stirring and the mixture is stirred thoroughly at 0° C. for 15 minutes. 70 g (0.5 mol) of solid 3-amino-benzoic acid are then introduced at the same temperature, the mixture is stirred for 15 minutes and heated up, and the solution formed is kept at 70° C. overnight. It is then evaporated, ethyl acetate and ice-water are added to the residue and the pH is brought to 7.5 by addition of saturated sodium bicarbonate solution. The product is extracted with ethyl acetate and the extracts are washed with water, dried over sodium sulfate and evaporated. 69.8 g (92.2%) of the pure methyl ester result in the form of an oil which crystallizes on standing; melting point 37–38° C.

Example 6:
Methyl 3-thioureido-benzoate 11.3 g of methyl 3-aminobenzoate are initially introduced into the reaction vessel as a solution in 75 ml of chlorobenzene, 2.07 ml of concentrated sulfuric acid (96%) are added dropwise at −5 to 0° C. in the course of 15 minutes, stirring is continued for 5 minutes, 6.8 g of sodium thiocyanate are then introduced in portions at a maximum of 0° C. and the mixture is stirred for a further 15 minutes. 0.2 ml of 15-crown-5 is then added, the mixture is stirred at a bath temperature of 100° C. for 10 hours and cooled and the precipitate formed is filtered off and washed 3 times with water. 13.5 g (85.9%) of the title compound of melting point 171–172° C. result.

Example 7:
Methyl 2-aminobenzothiazole-7-carboxylate 8.4 g of methyl 3-thioureido-benzoate are suspended in 120 ml of chlorobenzene, 2.2 ml of bromine in 30 ml of chlorobenzene are added at 0° C. in the course of 1 hour, while stirring as thoroughly as possible, and the mixture is then stirred to room temperature. It is then kept at 70° C. for 4 hours and subsequently cooled, a little diethyl ether is added and the precipitate is filtered off, mixed thoroughly with 70 ml of aqueous sodium bicarbonate solution, filtered off again and washed with water. 7.7 g (88%) of crude product of melting point 231–232° C. result. HPLC analysis shows a content of more than 83% of the pure title compound, in addition to 8–18% of isomeric methyl 2-amino-benzothiazole-5-carboxylate. Suspension in and brief heating at 70° C. with ethyl acetate, cooling to 30° C. and filtration give the pure title compound of melting point >250° C.
If the reaction is carried out in acetic acid (instead of in chlorobenzene), the content of the undesired isomeric methyl 2-amino-benzothiazole-5-carboxylate is only about 5%.

Example 8:
Direct preparation of benzo-1,2,3-thiadiazole-7-carboxylic acid from methyl 2-aminobenzothiazole-7-carboxylate

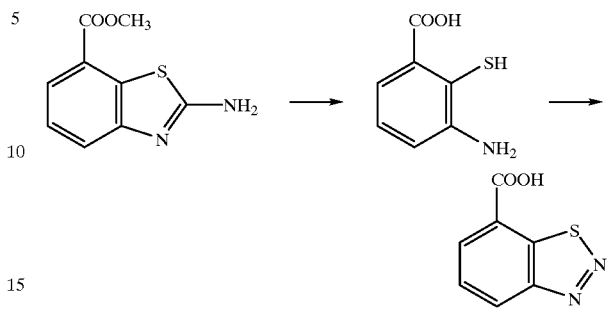

1.3 kg of methyl 2-aminobenzothiazole-7-carboxylate are kept at 120° C./1–2 bar in 3.5 kg of KOH 50% for 4 hours and the mixture is then neutralized with aqueous hydrochloric acid at 0 to 50° C. An aqueous solution of sodium nitrite 40% is metered into this solution at 0° C. to +10° C. and the product which has precipitated out is filtered off, washed and dried: 1.03 kg of benzo-1,2,3-thiadiazole-7-carboxylic acid, melting point 230–233° C. (91% of theory over the 2 stages).

Example 9:
Direct Preparation of Benzo-1,2,3-thiadiazole-7-carboxylic Acid from 2-methylamino-benzothiazole-7-carboxylic Acid

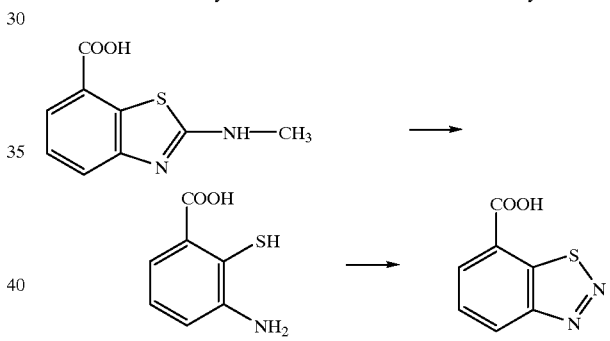

A suspension of 150 g of 2-methylaminobenzothiazole-7-carboxylic acid (92.7%) and 596 g of 47% KOH is kept at 155° C./1.7–1.8 bar in an autoclave for 12 hours and is then clarified by filtration at 20–25° C. The filtrate is added dropwise to 635 g of 37% hydrochloric acid and 50 ml of methanol are added. 200 g of 30% aqueous sodium nitrite solution are added dropwise to the suspension at −10° to −5° C. and the mixture is allowed to react completely at −5° to 0° C. for 2 hours. Filtration with suction and washing with water gives 112 g of crude benzo-1,2,3-thiadiazole-7-carboxylic acid of melting point 260–262° C. HPLC analysis shows a content of 90–93% of the pure title compound.

Example 10:
Preparation of 3-amino-2-mercaptobenzoic Acid 1.3 g of methyl 2-amino-7-methoxycarbonylbenzoate are introduced into 3.4 g of potassium hydroxide solution 50% under a nitrogen atmosphere and while stirring and the mixture is kept in a bomb tube at 120° C. for 12 hours. It is then cooled, a further 1.3 g of potassium hydroxide solution 50% are added under an inert atmosphere and the mixture is kept at 150° C. for another 4 hours. It is then cooled and added dropwise, under an inert atmosphere at 0° C., to an amount of dilute sulfuric acid such that a pH of 5.5 results.

The precipitate which forms is filtered off and washed with ice-water. After drying under a high vacuum, the title compound of melting point 255–258° C., which contains traces of the corresponding disulfide on the basis of the mass spectrum, results.

Example 11:

Preparation of 3-(N'-methyl-thioureido)-benzoic Acid

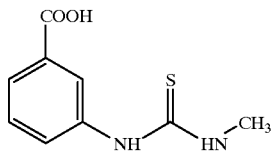

A mixture of 279.6 g of 3-amino-benzoic acid, 164.1 g of methyl isothiocyanate and 1000 g of 100% acetic acid is heated to 80–85° C. The temperature rises to 95–100° C. in the course of 20 minutes without further heating, and a clear solution from which the product slowly crystallizes out forms. The suspension is kept at 90–100° C. for 2 hours, subsequently cooled to 15–20° C. and filtered with suction and the material on the suction filter is washed with acetic acid. 404 g of the title compound result, purity: 99.5%, melting point: 190–91° C., decomposition. Yield: 95.7% of theory.

Example 12:

Preparation of 2-methylamino-benzothiazole-7-carboxylic Acid

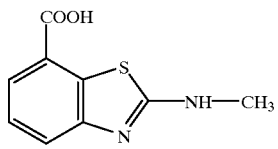

A solution of 163 g of bromine and 50 g of 100% acetic acid is added dropwise to a suspension of 212 g of 3-(N'-methylthioureido)-benzoic acid and 500 g of 100% acetic acid at 45–50° C. in the course of 2 hours. The mixture is then heated to 90–100° C. in the course of 2.5 hours and is allowed to react for a further 2 hours until the release of the gas has ended. After 150 g of acetic acid have been distilled off at 80–85° C. under reduced pressure, 200 g of water are added and the mixture is brought to pH 2 by dropwise addition of 30% sodium hydroxide solution. Filtration with suction at 70–80° C. and washing with water gives 179.2 g of the title compound of melting point: >330° C. HPLC analysis shows a content of 94.6% of the title compound, in addition to 3–4% of isomeric 2-methylamino-benzothiazole-5-carboxylic acid. Yield: 81.5% of theory.

Example 13:

Preparation of 2-methylamino-benzothiazole-7-carboxylic Acid Without Isolation of the Intermediate Product (One-pot Reaction)

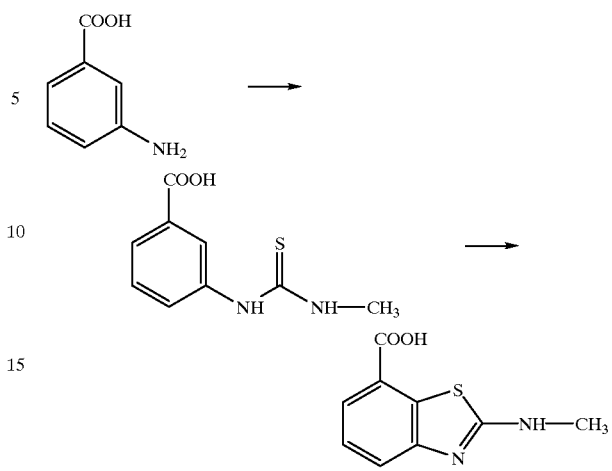

A solution of 39.2 g of methyl isothiocyanate and 50 g of 100% acetic acid is added dropwise to a suspension of 70 g of 3-amino-benzoic acid and 250 g of 100% acetic acid at 75–80° C. in the course of 50 minutes. A solution from which 3-(N'-methylthioureido)-benzoic acid slowly precipitates out in crystalline form is temporarily formed. After the mixture has been allowed to react completely for 2 hours, it is cooled to 50° and a solution of 81.5 g of bromine and 50 g of 100% acetic acid is added dropwise at 45–50° C. in the course of 2 hours. The mixture is then heated to 90–100° C. in the course of 2 hours and allowed to react completely for 2 hours, until the release of gas has ended. After 160 g of acetic acid have been distilled off at 75–80° C. under reduced pressure, 200 g of water have been added to the residue, 67 g of 30% sodium hydroxide solution have been added dropwise, the mixture has been filtered with suction at 75–80° C. and the residue has been washed with water, 73 g of product of melting point >330° C. are obtained. HPLC analysis shows a content of 97% of the title compound, in addition to 0.7% of isomeric 2-methylamino-benzothiazole-5-carboxylic acid. Yield: 68% of theory.

Example 14:

Methyl 3-amino-2-mercaptobenzoate

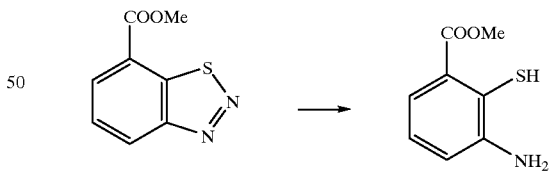

A solution of 1 g of methyl benzo-1,2,3-thiadiazole-7-carboxylate in 40 ml of dioxane is hydrogenated over 0.5 g of palladium-on-charcoal (5%) at 160° C under an initial pressure of 150 bar. After the starting substance has reacted completely, the catalyst is filtered off and rinsed with dioxane, the filtrate is evaporated, avoiding contact with air, and the residue is purified over silica gel (hexanelethyl acetate (6:4)). The title compound of melting point 174–175° C. is obtained by this procedure.

The compounds listed in the following tables can be prepared in a manner analogous to that described in the examples.

TABLE 1

Compounds of the formula $$\text{(X)}_n\text{-benzene with Z, SH, NH}_2 \text{ substituents}$$

| Compound No. | $(X)_n$ | Z | Physical data/melting point |
|---|---|---|---|
| 1.1 | 4-F | COOCH$_3$ | |
| 1.2 | 5-F | COOCH$_3$ | |
| 1.3 | 6-F | COOCH$_3$ | 125–127° C. (disulfide) |
| 1.4 | 4,6-di-F | COOCH$_3$ | |
| 1.5 | 4,5-di-F | COOCH$_3$ | |
| 1.6 | 5,6-di-F | COOCH$_3$ | |
| 1.7 | 4,5,6-tri-F | COOCH$_3$ | |
| 1.8 | H | COOCH$_3$ | 174–175° C. |
| 1.9 | H | COOC$_2$H$_5$ | |
| 1.10 | H | COOC$_3$H$_7$-n | |
| 1.11 | H | COOC$_3$H$_7$-i | |
| 1.12 | H | COOC$_6$H$_{13}$-n | |
| 1.13 | 4-F | COOC$_2$H$_5$ | |
| 1.14 | 6-F | COOC$_2$H$_5$ | |
| 1.15 | 5-F | COOC$_2$H$_5$ | |
| 1.16 | H | COSCH$_3$ | |
| 1.17 | H | CN | |
| 1.18 | H | COOH | 255–258° C. |
| 1.19 | 4-F | COOH | |
| 1.20 | 5-F | COOH | |
| 1.21 | 6-F | COOH | |
| 1.22 | 4,6-di-F | COOH | |
| 1.23 | 4,5,6-tri-F | COOH | |
| 1.24 | 5-F | CN | |
| 1.25 | H | COO— K+ | |

TABLE 2

Compounds of the formula benzothiazole with Z and NH—T substituents

| Compound No. | $(X)_n$ | Z | T | Physical data |
|---|---|---|---|---|
| 2.1 | 4-F | COOCH$_3$ | H | Melting point 263–264° C. |
| 2.2 | 5-F | COOCH$_3$ | H | |
| 2.3 | 6-F | COOCH$_3$ | H | |
| 2.4 | 4,6-di-F | COOCH$_3$ | H | |
| 2.5 | 4,5-di-F | COOCH$_3$ | H | |
| 2.6 | 5,6-di-F | COOCH$_3$ | H | |
| 2.7 | 4,5,6-tri-F | COOCH$_3$ | H | |
| 2.8 | H | COOCH$_3$ | H | Melting point > 250° C. |
| 2.9 | H | COOC$_2$H$_5$ | CH$_3$ | |
| 2.10 | H | COOC$_3$H$_7$-n | tert-butyl | |
| 2.11 | H | COOC$_3$H$_7$-i | H | |
| 2.12 | H | COOC$_6$H$_{13}$-n | H | |
| 2.13 | 4-F | COOC$_2$H$_5$ | H | |
| 2.14 | 6-F | COOC$_2$H$_5$ | H | |
| 2.15 | 5-F | COOC$_2$H$_5$ | H | |
| 2.16 | H | COSCH$_3$ | H | |
| 2.17 | 4-F | COSCH$_3$ | H | |
| 2.18 | H | COOH | CH$_3$ | Melting point > 330° C. |
| 2.19 | H | COOH | C$_2$H$_5$ | |
| 2.20 | H | COOH | i-propyl | |
| 2.21 | 6-F | COOH | CH$_3$ | |
| 2.22 | H | COOH | benzyl | |
| 2.23 | 4,5,6-tri-F | COOH | H | |
| 2.24 | 5-F | CN | H | |
| 2.25 | H | CN | H | |

TABLE 3

Compounds of the formula benzothiadiazole with Z substituent

| Compound No. | $(X)_n$ | Z | Physical data |
|---|---|---|---|
| 3.1 | 4-F | COOCH$_3$ | Melting point 133–134° C. |
| 3.2 | 5-F | COOCH$_3$ | |
| 3.3 | 6-F | COOCH$_3$ | Melting point 122–125° C. |
| 3.4 | 4,6-di-F | COOCH$_3$ | |
| 3.5 | 4,5-di-F | COOCH$_3$ | |
| 3.6 | 5,6-di-F | COOCH$_3$ | |
| 3.7 | 4,5,6-tri-F | COOCH$_3$ | |
| 3.8 | H | COOCH$_3$ | |
| 3.9 | H | COOC$_2$H$_5$ | |
| 3.10 | H | COOC$_3$H$_7$-n | |
| 3.11 | H | COOC$_3$H$_7$-i | |
| 3.12 | H | COOC$_6$H$_{13}$-n | |
| 3.13 | 4-F | COOC$_2$H$_5$ | |
| 3.14 | 6-F | COOC$_2$H$_5$ | |
| 3.15 | 5-F | COOC$_2$H$_5$ | |
| 3.16 | H | COSCH$_3$ | Melting point 131–132° C. |
| 3.17 | 4-F | COSCH$_3$ | Melting point 138–140° C. |
| 3.18 | H | COOH | Melting point 232–233° C. |
| 3.19 | 4-F | COOH | Melting point 224–226° C. |
| 3.20 | 5-F | COOH | Melting point 232–235° C. |
| 3.21 | 6-F | COOH | Melting point 222–223° C. |
| 3.22 | 4,6-di-F | COOH | |
| 3.23 | 4,5,6-tri-F | COOH | |
| 3.24 | 5-F | CN | |
| 3.25 | 4-F | CO—Cl | Melting point 75–78° C. |

TABLE 4

Compounds of the formula

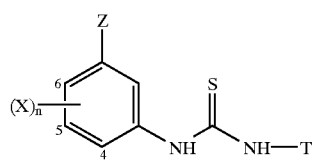

| Compound No. | (X)$_n$ | Z | T | Physical Data |
|---|---|---|---|---|
| 4.1 | 4-F | COOCH$_3$ | H | Melting point 163–165° C. |
| 4.2 | 5-F | COOCH$_3$ | H | |
| 4.3 | 6-F | COOCH$_3$ | H | |
| 4.4 | 4,6-di-F | COOCH$_3$ | H | |
| 4.5 | 4,5-di-F | COOCH$_3$ | H | |
| 4.6 | 5,6-di-F | COOCH$_3$ | H | |
| 4.7 | 4,5,6-tri-F | COOCH$_3$ | H | |
| 4.8 | H | COOCH$_3$ | H | Melting point 171–172° C. |
| 4.9 | H | COOC$_2$H$_5$ | H | |
| 4.10 | H | COOC$_3$H$_7$-n | CH$_3$ | |
| 4.11 | H | COOC$_3$H$_7$-i | tert-butyl | |
| 4.12 | H | COOC$_6$H$_{13}$-n | H | |
| 4.13 | 4-F | COOC$_2$H$_5$ | H | |
| 4.14 | 6-F | COOC$_2$H$_5$ | H | |
| 4.15 | 5-F | COOC$_2$H$_5$ | H | |
| 4.16 | H | COSCH$_3$ | H | |
| 4.17 | 4-F | COSCH$_3$ | H | |
| 4.18 | H | COOH | CH$_3$ | Melting point 190–191° C. |
| 4.19 | 4-F | COOH | CH$_3$ | |
| 4.20 | 5-F | COOH | C$_2$H$_5$ | |
| 4.21 | 6-F | COOH | i-propyl | |
| 4.22 | 4,6-di-F | COOH | CH$_3$ | |
| 4.23 | 4,5,6-tri-F | COOH | benzyl | |
| 4.24 | 5-F | CN | H | |
| 4.25 | H | CHO | H | |

TABLE 5

Compounds of the formula VI

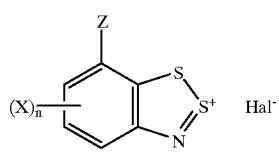

| Compound No. | X | Z | Hal | Physical data |
|---|---|---|---|---|
| 5.1 | H | COOH | Cl | >250° C. |
| 5.2 | H | COOCH$_3$ | Cl | |
| 5.3 | H | COOC$_2$H$_5$ | Cl | |
| 5.4 | H | COCl | Cl | |
| 5.5 | H | CHO | Cl | |
| 5.6 | H | COOH | F | |
| 5.7 | 6-F | COOH | F | |
| 5.8 | 6-F | COCl | Cl | |
| 5.9 | H | COOC$_3$H$_7$-n | Cl | |
| 5.10 | 6-Br | COOH | Br | |
| 5.11 | H | COSCH$_3$ | Cl | |
| 5.12 | H | COSC$_2$H$_5$ | Cl | |
| 5.13 | H | CN | Cl | |
| 5.14 | 6-Cl | COOH | Cl | |
| 5.15 | 6-F | CN | F | |
| 5.16 | 4-F | COOH | Cl | |
| 5.17 | 5-F | COOCH$_3$ | Cl | |
| 5.18 | 4,6-di-F | COOCH$_3$ | Cl | |
| 5.19 | 4,5,6-tri-F | COOH | Cl | |
| 5.20 | 6-Br | COOCH$_3$ | Cl | |

TABLE 5-continued

Compounds of the formula VI

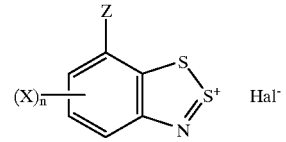

| Compound No. | X | Z | Hal | Physical data |
|---|---|---|---|---|
| 5.21 | H | COOCH$_3$ | ClO$_4$ | |
| 5.22 | H | COOH | ClO$_4$ | |
| 5.23 | H | COOH | BF$_4$ | |

TABLE 6

Compounds of the formula VII

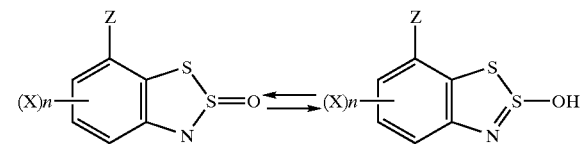

| Compound No. | X | Z | Physical Data |
|---|---|---|---|
| 6.1 | H | COOH | >290° C. |
| 6.2 | H | COOCH$_3$ | |
| 6.3 | H | COOC$_2$H$_5$ | |
| 6.4 | H | COCl | |
| 6.5 | H | CHO | |
| 6.6 | H | COOH | |
| 6.7 | 6-F | COOH | |
| 6.8 | 6-F | COCl | |
| 6.9 | H | COOC$_3$H$_7$-n | |
| 6.10 | 6-Br | COOH | |
| 6.11 | H | COSCH$_3$ | |
| 6.12 | H | COSC$_2$H$_5$ | |
| 6.13 | H | CN | |
| 6.14 | 6-Cl | COOH | |
| 6.15 | 6-F | CN | |
| 6.16 | 4-F | COOH | |
| 6.17 | 5-F | COOCH$_3$ | |
| 6.18 | 4,6-di-F | COOCH$_3$ | |
| 6.19 | 4,5,6-tri-F | COOH | |
| 6.20 | 6-Br | COOCH$_3$ | |

What is claimed is:

1. A compound of formula IV

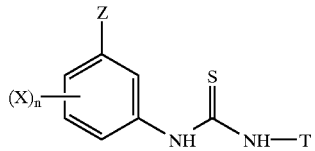

IV or salt thereof, in which:

X is fluorine;

n is 0, or 1;

T is hydrogen or $C_1$–$C_6$alkyl;

Z is CO—A;

A is OR$_1$, or SR$_2$;

R$_1$ and R$_2$ are hydrogen, a substituted, open chain, saturated or unsaturated hydrocarbon radical containing not more than 8 carbon atoms, a substituted or unsubstituted cyclic, saturated or unsaturated hydrocarbon radical containing not more than 10 carbon atoms, substituted or unsubstituted benzyl or phenethyl, a substituted or unsubstituted alkanoyl group or a substituted or unsubstituted heterocyclyl radical; or $R_3$ and $R_4$, together with the nitrogen atom to which they are bonded, are a 5- or 6-membered substituted or unsubstituted heterocyclic radical having 1–3 heteroatoms O,S, and/or N;

with the exception of the compound in which Z is $COOC_2H_5$, n is 0 and T is hydrogen.

2. A compound of claim 1, in which n is 0.

3. A compound of claim 1, in which A is $OR_1$.

4. A compound of claim 3 in which $R_1$ is hydrogen.$C_1$–$C_6$alkyl, which is unsubstituted or substituted by 1–3 halogen atoms, or $C_1$–$C_2$alkoxy, $C_3$–$C_6$cycloalkyl, or phenyl, benzyl or phenethyl, the phenyl rings of which are unsubstituted or substituted once or twice by halogen, hydroxy, $C_1$–$C_4$alkyl, halogeno-$C_1$–$C_2$alkyl, $C_1$–$C_2$alkoxy, halogeno-$C_1$–$C_2$alkoxy or nitro.

5. A compound of claim 1 in which A is $SR_2$.

6. A compound of claim 5 in which $R_2$ is hydrogen.$C_1$–$C_6$alkyl, which is unsubstituted or substituted by 1–3 halogen atoms, or $C_1$–$C_2$alkoxy, $C_3$–$C_6$cycloalkyl, or phenyl, benzyl or phenethyl, the phenyl rings of which are unsubstituted or substituted once or twice by halogen, hydroxy, $C_1$–$C_4$alkyl, halogeno-$C_1$–$C_2$alkyl, $C_1$–$C_2$alkoxy, halogeno-$C_1$–$C_2$alkoxy or nitro.

7. A compound of claim 1 of the formula A

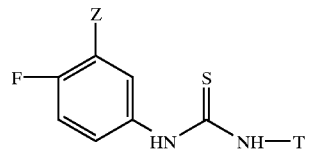

or salt thereof.

8. A compound of claim 7 in which A is $OR_1$.

9. A compound of claim 7 in which $R_1$ is hydrogen.$C_1$–$C_6$alkyl, which is unsubstituted or substituted by 1–3 halogen atoms, or $C_1$–$C_2$alkoxy, $C_3$–$C_6$cycloalkyl, or phenyl, benzyl or phenethyl, the phenyl rings of which are unsubstituted or substituted once or twice by halogen, hydroxy, $C_1$–$C_4$alkyl, halogeno-$C_1$–$C_2$alkyl, $C_1$–$C_2$alkoxy, halogeno-$C_1$–$C_2$alkoxy or nitro.

10. A compound of claim 7 in which A is $SR_2$.

11. A compound of claim 10 in which $R_2$ hydrogen.$C_1$–$C_6$alkyl, which is unsubstituted or substituted by 1–3 halogen atoms, or $C_1$–$C_2$alkoxy, $C_3$–$C_6$cycloalkyl, or phenyl, benzyl or phenethyl, the phenyl rings of which are unsubstituted or substituted once or twice by halogen, hydroxy, $C_1$–$C_4$alkyl, halogeno-$C_1$–$C_2$alkyl, $C_1$–$C_2$alkoxy, halogeno-$C_1$–$C_2$alkoxy or nitro.

* * * * *